United States Patent [19]

Fields et al.

[11] 4,025,569

[45] May 24, 1977

[54] DIELS-ALDER ADDUCTS OF HEXAHALOCYCLOPENTADIENE AND DIALKYL-ALPHAMETHYLSTYRENE

[75] Inventors: Ellis K. Fields, River Forest; Alfred Steitz, Jr., deceased, late of Batavia, Ill., by Margaret Marie Steitz, executrix

[73] Assignee: Standard Oil Company (Indiana), Chicago, Ill.

[22] Filed: Apr. 7, 1975

[21] Appl. No.: 565,846

Related U.S. Application Data

[62] Division of Ser. No. 402,486, Oct. 1, 1973, Pat. No. 3,903,144.

[52] U.S. Cl. .......................... 260/649 R; 260/649 F
[51] Int. Cl.$^2$ .......................................... C07C 25/18
[58] Field of Search ........ 260/649 R, 648 C, 649 F

[56] References Cited

UNITED STATES PATENTS

| | | | |
|---|---|---|---|
| 2,606,910 | 8/1952 | Herzfeld et al. | 260/648 C |
| 2,901,510 | 8/1959 | Molotsky et al. | 260/648 C |
| 2,952,712 | 9/1960 | Roberts et al. | 260/649 R |

Primary Examiner—D. Horwitz
Attorney, Agent, or Firm—William H. Magidson; Arthur G. Gilkes; William T. McClain

[57] ABSTRACT

New chemical compounds useful as intermediates are 5-(1-methyl-3,4,5,6,7,7-hexahalo-norborn-4-ene-1)-isophthalic acid and 4-(1-methyl 3,4,5,6,7,7-hexahalo-norborn-4-ene-1)-orthophthalic acid, formed by oxidation of the primary or secondary alkyl groups containing from one to ten carbon atoms on the benzene ring of the Diels-Alder adduct of equimolecular amounts of hexahalocyclopentadiene and either 3,5-dialkyl-α-methyl-styrene and 3,4-dialkyl-α-methylstyrene. The acyl derivatives of these intermediates do not burn or support combustion and are also useful as extreme-pressure additives in lubricating oils. The following acyl derivatives of 5-(1-methyl-3,4,5,6,7,7-hexachloro-norborn-4-ene-1)-isophthalic acid have been prepared: the dichloride, diamide, dianilide, diethylester, polyphenylester, poly(chlorophenyl) ester, poly-ethylene glycol ester, diphenylthioester, di-methallylester, and unsaturated polyester. Also, the co-polyphenylesters of 5-(1-methyl-3,4,5,6,7,7-hexachloro-norborn-4-ene-1)-isophthalic acid and terephthalic or adipic acid; the polyamide of 5-(1-methyl-3,4,5,6,7,7-hexachloro-norborn-4-ene-1)-isophthalic acid and 1,6-hexanediamine; the copolyamides of 5-(1-methyl-3,4,5,6,7,7-hexachloronorborn-4-ene-1) isophthalic acid and 1,6-hexanediamine and terephthalic acid or adipic acid; the co-polyethylene glycol ester of 5-(1-methyl-3,4,5,6,7,7-hexachloro-norborn-4-ene-1) isophthalic acid and terephthalic acid; and a phosphorus adduct of 5-(1-methyl-3,4,5,6,7,7-hexachloro-norborn-4-ene-1) have been prepared.

5 Claims, No Drawings

DIELS-ALDER ADDUCTS OF HEXAHALOCYCLOPENTADIENE AND DIALKYL-ALPHAMETHYLSTYRENE

This is a division of application Ser. No. 402,486 filed Oct. 1, 1973 now U.S. Pat. No. 3,903,144.

BACKGROUND OF THE INVENTION

1. Field of the Invention

This invention relates to new organic acids obtained by oxidation of the adduct of hexahalocyclopentadiene and either 3,4-dialkyl-α-methylstyrene or 3,5-dialkyl-α-methylstyrene and to a method for making the same and pertains to acyl derivatives of said compounds.

Description of the Prior Art

It is known to prepare Diels-Alder reaction products of hexahalocyclopentadiene with unsaturated organic compounds. Herzfeld et al, U.S. Pat. No. 2,606,910 (1952) reacts styrene and hexachlorocyclopentadiene to obtain the corresponding polycyclic adduct of hexachlorocyclopentadiene and styrene in a mole ratio of 1:1. Roberts, U.S. Pat. No. 2,952,711 (1960) makes an adduct of hexachlorocyclopentadiene and divinylbenzene by reacting approximately equimolecular proportions of hexachlorocyclopentadiene and divinylbenzene. Roberts, U.S. Pat. No. 2,952,712 (1960) makes an adduct of hexachlorocyclopentadiene and a monovinyl aromatic compound selected from the group consisting of vinyltoluene, ar-ethylvinylbenzene, 4-tertbutylstyrene and 2,4-dichlorostyrene by reacting approximately equimolecular proportions of hexachlorocyclopentadiene and the monovinyl aromatic compound.

SUMMARY OF THE INVENTION

However, it has not heretofore been known to prepare the oxidized form of the Diels-Alder reaction product of hexahalocyclopentadiene and either 3,5-dialkyl-α-methylstyrene or 3,4-dialkyl-α-methylstyrene. The alkyl groups can be primary or secondary and can contain from one to ten carbon atoms. The adducts formed are 5-(1-methyl-3,4,5,6,7,7-hexahalo-norborn-4-ene-1)-isophthalic acid and 4-(1-methyl-3,4,5,6,7,7-hexahalo-norborn-4-ene-1)-orthophthalic acid respectively. By our invention, these compounds are readily prepared from available and inexpensive raw materials. They are useful as intermediates in the production of other new and valuable derivatives. Because of their high halogen content, such new derivatives do not burn or support combustion. These new derivatives are also useful as extreme-pressure additives in lubricating oils. For example, from the oxidized adducts we have made esters, amides, polyesters, and polyamides, all of which are new compounds, that are useful as non-flammable plasticizers, fiberformers, sheets, reinforced castings and moldings, pesticides, and lubricating-oil additives.

The method of formation of 5-(1-methyl-3,4,5,6,7,7-hexahalo-norborn-4-ene-1)-isophthalic acid and 4-(1-methyl-3,4,5,6,7,7-hexahalo-norborn-4-ene-1)-orthophthalic acid consists of two steps. The first step is adduct formation by reaction of hexahalocyclopentadiene and either 3,5-dialkyl-α-methylstyrene or 3,4-dialkyl-α-methylstyrene. The second step is oxidation of the product of the first step.

DESCRIPTION OF THE PREFERRED EMBODIMENTS

The hexahalocyclopentadiene starting material can be hexachlorocyclopentadiene or hexabromocyclopentadiene. If the alkyl substituents on the benzene ring of the α-methylstyrene starting material are methyl groups, then the 3,5-dimethyl-α-methylstyrene or 3,4-dimethyl-α-methylstyrene can be obtained by propylation of meta-xylene or ortho-xylene, respectively, followed by dehydrogenation. The alkyl groups can be primary or secondary alkyl groups and can contain from one to ten carbon atoms.

The first step of the method of this invention consists of reacting a mixture of hexahalocyclopentadiene and either 3,5-dialkyl-α-methylstyrene or 3,4-dialkyl-60-methylstyrene. The molecular ratio of the components of the mixture can range from about 1:5 to about 5:1. Preferably, equimolecular amounts of each component are used in the mixture. The components react 1:1 when the mixture is heated to a temperature in the range from 80° C. up to 180° C., for a period of time from 1 hour to 24 hours. The preferred ranges are a temperature between 135° C. and 160° C. and a reaction time between 3 hours and 15 hours.

The reaction pressure can be from 15 pounds per square inch to 300 pounds per square inch, and preferably 10 pounds per square inch.

The reaction is then continued by distilling the reaction mixture in vacuo at a pressure that can be in the range of from 0.1 millimeter up to 2 millimeters. The preferred range is from 0.5 millimeter up to 1 millimeter. The distillation is continued until the temperature of the liquid reaction mixture is from 85° C., and preferably at least 100° C., to 140° C., but usually not over 120° C. The adduct product crystallizes slowly. The adduct is recrystallized as white crystals from any nonpolar solvent, for example, hexane, benzene, carbon tetrachloride, toluene, or naphthalene. The recrystalized white crystals melt at 101° C. More particularly, the product of step one can be represented by the product produced in accordance with the following equation:

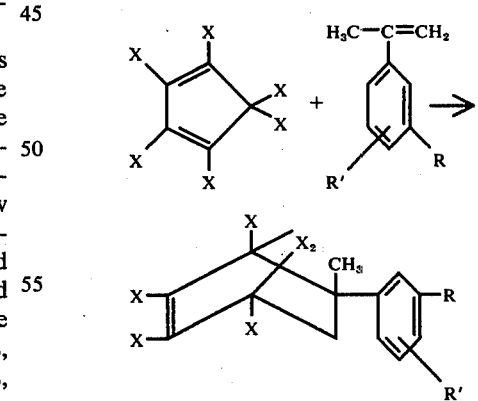

wherein X represents a bromine or chlorine atom and R and R' are primary or secondary alkyl groups containing from 1 to 10 carbon atoms.

The second step of the method consists of oxidizing the product of the first step. Solutions of aliphatic carboxylic acids containing 2 to 5 carbon atoms are particularly useful as the medium for such oxidation, preferably aliphatic carboxylic acids containing between 2 and 4 carbon atoms. The oxidation medium also contains salts of transition metals, preferably of cobalt, manganese, or cerium, to decompose hydroperoxides formed during the oxidation. In addition, the oxidation medium contains a source of bromide ions, preferably ammonium bromide, sodium bromide, potassium bromide, benzyl bromide, or 1,2,2-tribromoethane. The transition metals and bromide ions function as part of the catalyst for the reaction.

The oxidation can be effected by passing a stream of gas, preferably air, containing oxygen through the oxidation medium at a pressure from 15 pounds per square inch to 1000 pounds per square inch, for a period of time from one half hour to ten hours. The preferred ranges are a pressure from 200 pounds per square inch to 400 per square inch and a reaction time from 45 minutes to 90 minutes. Alternatively, the oxidation can be effected using any of the other well-known chemical oxidants, for example, potassium permanganate, potassium dichromate, sodium perchlorate, manganese dioxide and dilute nitric acid. The temperature at which the oxidation is performed can be from 100° C. to 325° C. The preferred range is 180° C. to 250° C.

The mixture of acid product and mother liquor is cooled, and the mixture is filtered to remove solid acid product. Additional acid product can be recovered from the mother liquor by distilling off 50–80 percent of the mother liquor to concentrate the solution and then chilling the remainder mother liquor to a temperature between 10° C. and −10° C. The mother liquor is then filtered to remove solid acid product which crystallizes during chilling. The total crude acid product yield from the second step of the method is about 100 percent.

The crude acid product is purified by dissolving it in a dilute solution of inorganic base, for example, sodium carbonate, sodium bicarbonate, or ammonium hydroxide, or organic base, including primary, secondary, or tertiary amines, for example, dimethylamine, trimethylamine or pyridine. Then the solution of acid product is treated with charcoal to remove color and filtered. The acid product is precipitated by acidifying the filtrate with an excess of an acid which is a stronger acid than the acid product, for example, dilute sulfuric acid or hydrochloric acid. The solid acid product is then filtered, washed, and dried. The acid product decomposes at 345° C. without melting.

The product 5-(1-methyl-3,4,5,6,7,7-hexahalo-norborn-4-ene-1)-isophthalic acid possesses the advantage over 4-(1-methyl-3,4,5,6,7,7-hexahalo-norborn-4-ene-1)-orthophthalic acid that its two carboxyl groups do not form an anhydride because they are in ring positions that are meta to one another. Further, the esters and amides of 5-(1-methyl-3,4,5,6,7,7-hexahalo-norborn-4-ene-1)-isophthalic acid are particularly thermally stable.

The following examples illustrate ways in which the principle of the invention has been applied, but are not to be construed as limiting its scope. In each example, elemental analysis was used to determine the composition of the product formed.

EXAMPLE I

A mixture of 129.3 milliliters (0.8 mole) of hexachlorocyclopentadiene and 166.4 grams (0.8 mole) of 3,5-dimethyl-α-methylstyrene (obtained from propylation of m-xylene and dehydrogenation) was heated at 152° C. for 15 hours, and then was distilled in vacuo until the temperature of the liquid was 110° C. at 0.8 milliliters. The residue slowly crystallized and weighted 284 grams constituting an 85% yield. It was recrystallized from n-hexane to give white crystals, melting at 101° C. of

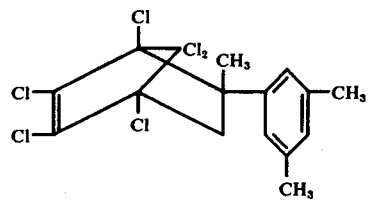

As shown in the following tabulation, the results of elemental analysis of the product compared very closely with the calculated elemental composition of $C_{16}H_{14}Cl_6$:

|  | C | H | Cl |
|---|---|---|---|
| Elemental analysis | 45.8 | 3.4 | 50.6 |
| Calculated elemental composition | 45.9 | 3.4 | 50.8 |

EXAMPLE II

A solution of 166 grams (0.397 mole) of the product of Example I in 1250 milliliters of acetic acid containing 33 grams of ammonium bromide, 8 grams of cobalt acetate, and 16 grams of manganese acetate was oxidized with air at 390 pounds per square inch and 400° F. The cooled mixture was filtered to give a cake weighing 136 grams; 56 grams of acid product was recovered from the mother liquor. The total crude yield was 100 percent. The acid, 5-(1-methyl-3,4,5,6,7,7-hexachloro-norborn-4-ene-1)-isophthalic acid, was purified by dissolving it in 5 percent aqueous sodium bicarbonate, treating with charcoal, filtering, and acidifying with an inorganic acid like dilute sulfuric acid, dilute hydrochloric acid, or dilute nitric acid. The precipitated acid was filtered, washed, and dried. It blackened at 345° C. without melting. As shown in the following tabulation, the results of elemental analysis of the product and experimental measurement of its acid number compared very closely with the corresponding values calculated for $C_{16}H_{10}O_4Cl_6$:

|  | C | H | Cl | acid number |
|---|---|---|---|---|
| Experimental determination | 40.1 | 2.2 | 44.0 | 230 |
| Calculated values | 40.2 | 2.1 | 44.4 | 234 |

EXAMPLE III

A mixture of 84 grams (0.1755 mole) of 5-(1-methyl-3,4,5,6,7,7-hexachloro-norborn-4-ene-1)-isophthalic acid and 180 milliliters (2.48 moles) of thionyl chloride, was stirred and refluxed for 96 hours, by which time all the solid had dissolved. The excess thionyl chloride, 162 milliliters was recovered by distillation at 33°– 40° C. and 140 millimeters of pressure. The residue was crystallized from n-hexane to give 83 grams, for a 92 percent yield of 5-(1-methyl-3,4,5,6,7,7-hexa-chloro-norborn-4-ene-1)-isophthalic acid dichloride:

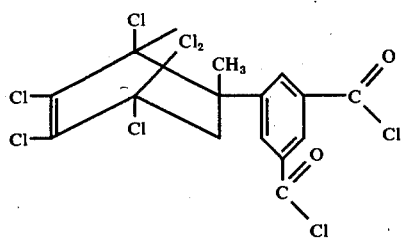

The product melted at 122° C. As shown in the following tabulation, the results of elemental analysis of the product compared very closely with the calculated elemental composition of $C_{16}H_8O_2Cl_8$:

|  | C | H | Cl |
|---|---|---|---|
| Elemental analysis | 37.2 | 1.6 | 54.9 |
| Calculated elemental composition | 37.3 | 1.6 | 55.0 |

EXAMPLE IV

A solution of 0.516 grams (0.001 mole) of 5-(1-methyl-3,4,5,6,7,7-hexachloro-norborn-4-ene-1)-isophthalic dichloride in 20 milliliters of n-hexane was stirred with 10 milliliters (0.1765 mole) of 30 percent aqueous ammonium hydroxide at 30° C. for 10 minutes. The solid was filtered, washed, and recrystallized from ethanol to give 0.45 grams, for a 95 -percent yield, of 5-(-methyl-3,4,5,6,7,7-hexachloro-norborn-4-ene-1)-isophthalic acid diamide:

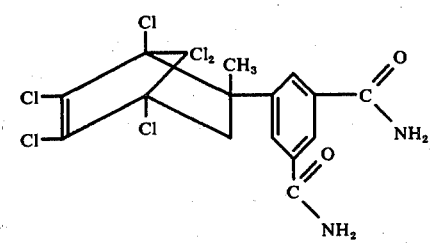

The product sintered at 158° C. and melted at 228° C. As shown in the following tabulation, the results of elemental analysis of the product compared very closely with the calculated elemental composition of $C_{16}H_{12}N_2O_2Cl_6$:

|  | C | H | N | Cl |
|---|---|---|---|---|
| Experimental analysis | 40.3 | 2.7 | 5.8 | 44.1 |
| Calculated elemental composition | 40.3 | 2.5 | 5.9 | 44.6 |

EXAMPLE V

A solution of 0.365 milliliters (.004 mole) of aniline in 20 milliliters of benzene was added to a solution of 0.516 grams (0.001 mole) of 5-(1-methyl-3,4,5,6,7,7-hexachloro-norborn-4-ene-1)-isophthalic acid dichloride in 20 milliliters of n-hexane at 25° C. with stirring. The white solid dianilide produced was filtered, washed with benzene and water, and dried:

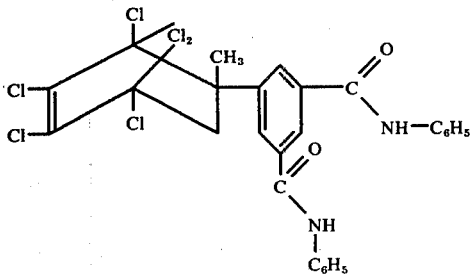

It weighed 0.63 grams, for a 100 percent yield, and after recrystallization from benzene, melted at 280° C.

As shown in the following tabulation, the results of elemental analysis of the product compared very closely with the calculated elemental composition of $C_{28}H_{20}N_2O_2Cl_6$:

|  | C | H | N | Cl |
|---|---|---|---|---|
| Experimental analysis | 53.2 | 3.6 | 4.1 | 33.4 |
| Calculated elemental composition | 53.4 | 3.2 | 4.5 | 33.8 |

EXAMPLE VI

A solution of 0.516 grams (0.001 mole) of 5-(1-methyl-3,4,5,6,7,7-hexachloro-norborn-4-ene-1)-isophthalic acid dichloride in 10 milliliters of absolute ethanol was refluxed for 2 hours, and then was evaporated. The solid diethyl ester product weighed 0.53 grams, for a 100 percent yield, and was recrystallized from n-hexane:

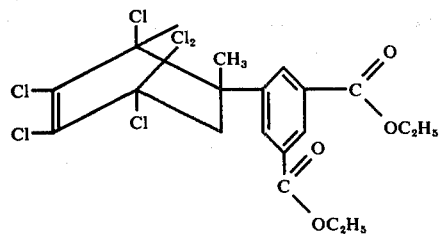

The product melted at 101° C. As shown in the following tabulation, the results of elemental analysis of the product compared very closely with the calculated elemental composition of $C_{20}H_{18}O_4Cl_6$:

|  | C | H | Cl |
|---|---|---|---|
| Elemental analysis | 44.7 | 3.5 | 39.6 |
| Calculated elemental composition | 44.8 | 3.4 | 39.8 |

EXAMPLE VII

To prepare a polyphenylester of 5-(1-methyl-3,4,5,6,7,7-hexachloro-norborn-4-ene-1)-isophthalic acid, a solution of 0.516 grams (0.001 mole) of 5-(1-methyl-3,4,5,6,7,7-hexachloro-norborn-4-ene-1)-isophthalic acid dichloride in 20 milliliters of n-hexane was added with rapid stirring in a Waring blender to a solution of 0.241 grams (0.001 mole) of Bisphenol B (p,p'-sec.-butylidene diphenol) in 40 milliliters of 1 Molar sodium hydroxide. The polyphenylester was collected on a filter, washed, and dried. The recovered product weighed 0.67 grams, for a 97 percent yield, and melted at 254° C.

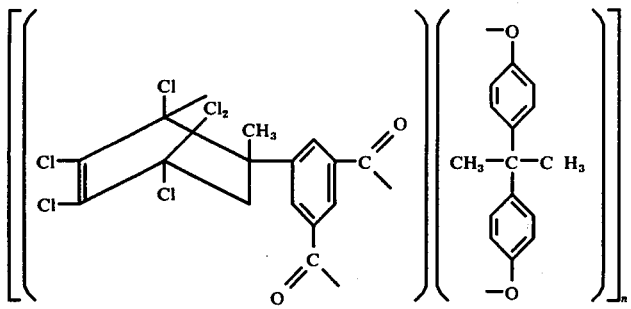

As shown in the following tabulation, the results of elemental analysis of the product compared very closely with the calculated elemental composition of $(C_{32}H_{24}O_4Cl_6)_n$, wherein n can range from 3 to 100 depending on the conditions:

|  | C | H | Cl |
| --- | --- | --- | --- |
| Elemental analysis | 57.1 | 2.5 | 30.5 |
| Calculated elemental composition | 56.1 | 3.5 | 31.1 |

EXAMPLE VIII

To prepare a poly (chlorophenyl) ester of 5-(1-methyl-3,4,5,6,7,7-hexachloro-norborn-4-ene-1)-isophthalic acid, a solution of 0.516 grams (.001 mole) of 5-(1-methyl-3,4,5,6,7,7-hexachloro-norborn-4-ene-1)-isophthalic acid dichloride in 20 milliliters of hexane was added to a solution of 0.297 grams (0.001 mole) of dichloro Bisphenol A,

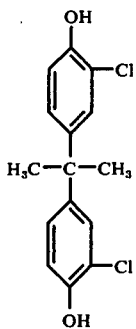

in 40 milliliters of 1 Molar sodium hydroxide with rapid stirring in a Waring blender at 25° C. The polymer was washed and dried. The product weighed 0.36 grams for a 49 percent yield. Its melting point was 286°–290° C.

As shown in the following tabulation, the results of elemental analysis of the product compared very closely with the calculated elemental composition for $C_{13}H_{20}O_4Cl_8$:

|  | C | H | Cl |
| --- | --- | --- | --- |
| Elemental analysis | 50.6 | 2.7 | 38.0 |
| Calculated elemental composition | 50.3 | 2.7 | 38.4 |

EXAMPLE IX

To prepare a co-polyphenylester of 5-(1-methyl-3,4,5,6,7,7-hexachloro-norborn-4-ene-1)-isophthalic acid and terephthalic acid, a solution of 0.516 grams (0.001 mole) of 5-(1-methyl-3,4,5,6,7,7-hexachloro-norborn-4-ene-1)-isophthalic acid dichloride and 0.8132 grams (0.004 mole) of terephthaloyl chloride in 20 milliliters of benzene was added to a solution of 1.205 grams (0.005 mole) of Bisphenol B in 40 milliliters of 1 Molar sodium hydroxide in a Waring blender at 30° C. The white copolymer was filtered, washed, and dried. The product weighed 2.05 grams for a 95 percent yield. Its melting point was 280° C.

EXAMPLE X

To prepare a co-polyphenyl ester of 5-(1-methyl-3,4,5,6,7,7-hexachloro-norborn-4-ene-1)-isophthalic acid and adipic acid, a solution of 0.516 grams (0.001 mole) of 5-(1-methyl-3,4,5,6,7,7-hexachloro-norborn-4-ene-1(-isophthalic acid dichloride and 0.732 grams (0.004 mole) of adipoyl chloride in 25 milliliters of n-hexane was added to a solution of 1.205 grams (0.005 mole) of Bisphenol B in 40 milliliters of 1 Molar sodium hydroxide in a Waring blender at 30° C. The white copolymer was filtered, washed and dried. The product weighed 2.0 grams for a yield of 96 percent. It melted at 178° C.

EXAMPLE XI

To prepare the poly(1,6-hexane) amide of 5-(1-methyl-3,4,5,6,7,7-hexachloro-norborn-4-ene-1)-isophthalic acid, a solution of 0.516 grams (0.001 mole) 5-(1-methyl-3,4,5,6,7,7-hexachloro-norborn-4-ene-1)-isophthalic acid dichloride in 25 milliliters of of n-hexane was added to a solution of 0.12 grams (0.001 mole) of 1,6-hexanediamine in 40 milliliters of 1 Molar sodium hydroxide in a Waring blender. The polyamide was filtered, washed, and dried. The product weighed 0.17 grams for a yield of 48 percent. Upon heating, the product darkened at 280° C. and melted at 308° C. As shown in the following tabulation, the results of elemental analysis of the product compared very closely with the calculated elemental composition of $(C_{22}H_{22}O_2Cl_6N_2)_m$ where m can be 3 to 100 depending on the conditions used;

|  | C | H | Cl | N |
| --- | --- | --- | --- | --- |
| Elemental analysis | 46.8 | 4.2 | 37.7 | 5.4 |
| Calculated elemental composition | 47.3 | 3.9 | 38.1 | 5.0 |

EXAMPLE XII

To prepare a copolyamide of 5-(1-methyl-3,4,5,6,7,7-hexachloro-norborn-4-ene-1)-isophthalic acid and terephthalic acid, a solution of 0.516 grams (0.001 mole) of 5-(1-methyl-3,4,5,6,7,7-hexachloro-norborn-4-ene-1)-isophthalic acid dichloride and 0.8132 grams (0.004 mole) of terephthaloyl chloride in 40 milliliters of benzene was added to 0.6 grams (0.005 mole) of 1,6-hexanediamine in 40 milliliters of 1 Molar sodium hydroxide in a Waring blender. The copolyamide was filtered, washed, and dried. The product weighed 1.42 grams for a 91 percent yield and melted at 294° C. It was fibrous like asbestos.

EXAMPLE XIII

To prepare a copolyamide of 5-(1-methyl-3,4,5,6,7,7-hexachloro-norborn-4-ene-1)-isophthalic acid and adipic acid, a solution of 0.516 grams (0.001 mole) of 5-(1-methyl-3,4,5,6,7,7-hexachloro-norborn-4-ene-1)-isophthalic acid dichloride and 0.732 grams (0.004 mole) of adipoyl chloride in 25 milliliters of n-hexane was added at 25° C. to 0.6 grams (0.005 mole) of 1,6-hexanediamine in 40 milliliters of 1 Molar sodium hydroxide in a Waring blender. The copolyamide was filtered, washed, and dried. The product weighed 1.36 grams for a 92 percent yield and melted at 255° C.

EXAMPLE XIV

To prepare the poly-ethylene glycol ester of 5-(1-methyl-3,4,5,6,7,7-hexachloro-norborn-4-ene-1)-isophthalic acid, a mixture of 0.516 grams (0.001 mole) of 5-(1-methyl-3,4,5,6,7,7-hexachloro-norborn-4-ene-1)-isophthalic acid dichloride and 10 milliliters of a solution of 0.62 grams (0.01 mole) of ethylene glycol in 100 milliters of 1,2-dimethoxy ethane containing 0.001 mole of ethylene glycol was refluxed under dry nitrogen for 4 hours, then evaporated in a stream of dry nitrogen and heating continued for 3 hours at 150° C. The polymer weighed 0.482 grams for a 95 percent yield and melted at 266°–267° C. As shown in the following tabulation, the results of elemental analysis of product compared very closely with the calculated elemental composition of $(C_{18}H_{12}O_4Cl_6)_m$ where m can be 3 to 100 depending on the conditions used:

|  | C | H | Cl |
|---|---|---|---|
| Elemental analysis | 42.6 | 2.7 | 41.5 |
| Calculated elemental composition | 42.8 | 2.4 | 42.1 |

EXAMPLE XV

To prepare the co-polyethylene glycol ester of 5-(1-methyl-3,4,5,6,7,7-hexachloro-norborn-4-ene-1)-isophthalic acid and terephthalic acid, a solution of 0.516 grams (0.001 mole) of 5-(1-methyl-3,4,5,6,7,7-hexachloro-norborn-4-ene-1)-isophthalic acid dichloride and 0.8132 grams (0.004 mole) of terephthaloyl chloride in 5 milliliters of 1,2-dimethoxy ethane containing 0.37 grams (0.005 mole) of ethylene glycol was refluxed 24 hours, then evaporated under a stream of dry nitrogen. Heating under nitrogen was continued for 4 hours at 150° C. to give 1.54 grams, or a yield of 96 percent, of copolymer melting at 288°–290° C.

EXAMPLE XVI

To prepare the di-phenylthioester of 5-(1-methyl-3,4,5,6,7,7-hexachloro-norborn-4-ene-1)-isophthalic acid, a solution of 2.068 grams (0.004 mole) of 5-(1-methyl-3,4,5,6,7,7-hexachloro-norborn-4-ene-1)-isophthalic dichloride in 5.5 grams (0.05 mole) of benzenethiol was heated at 135° C. for 4 hours, then evaporated on the steam bath. The product

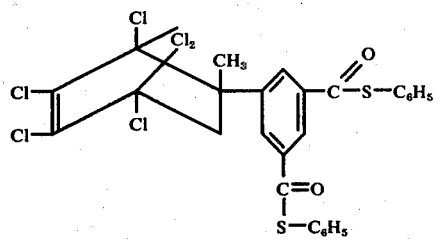

weighed 3.4 grams for a yield of 98 percent and melted at 196° C. after crystallization from ethanol.

EXAMPLE XVII

To prepare the di-methallyl ester of 5(1-methyl-3,4,5,6,7,7-hexachloro-norborn-4-ene-1)-isophthalic acid, a solution of 5.61 grams (0.01 mole) of 5-(1-methyl-3,4,5,6,7,7-hexachloro-norborn-4-ene-1)-isophthalic dichloride in 7.2 grams (0.1 mole) of methallyl alcohol was refluxed with 8 milliliters (0.1 mole) of pyridine for 10 minutes. The cooled mixture was poured into water; the heavy layer was extracted with 50 milliliters of carbon tetrachloride, washed, dried, and evaporated on the steam bath, giving 6.2 grams, or a 98 percent yield of light yellow, viscous di-methallyl ester.

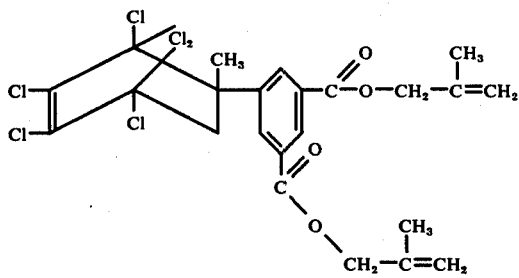

As shown in the following tabulation, the results of elemental analysis of the product compared very closely with the calculated elemental composition of $C_{24}H_{22}O_4Cl_6$:

|  | C | H | Cl |
|---|---|---|---|
| Elemental analysis | 48.6 | 3.8 | 33.0 |
| Calculated elemental Composition | 49.1 | 3.8 | 36.2 |

EXAMPLE XVIII

A 0.5 gram sample of this ester, heated with 0.01 grams of benzoyl peroxide at 100° C. for 70 hours, gave a brittle, yellow resin.

To prepare a phosphorus derivative of 5-(1-methyl-3,4,5,6,7,7-hexachloro-norborn-4-ene-1)-isophthalic acid, a solution of 4.5 grams (0.0072 mole) of the di-methallyl ester of Example XVII in 20 milliliters of toluene was stirred and refluxed for 4 hours with 1.506 grams (0.0072 mole) of phosphorus pentasulfide. The cooled mixture was filtered and evaporated, giving 5 grams of reddish, very viscous phosphorus adduct. The results of elemental analysis are 26.4% and 9.5% S.

EXAMPLE XIX

As unsaturated polyester of 5-(1-methyl-3,4,5,6,7,7-hexachloro-norborn-4-ene-1)-isophthalic acid was prepared by heating a mixture of 2.14 grams (0.004 mole) of the diethyl ester of 5-(1-methyl-3,4,5,6,7,7-hexachloro-norborn-4-ene-1)-isophthalic acid, the product of Example VI, 1.24 grams (0.02 mole) of ethylene glycol, and 1.56 grams (0.016 mole) of maleic anhydride at 150°–180° C. under dry nitrogen for 3 hours. Heating was continued at 185° C. under 100 milliliters of pressure for 2 hours, giving 4.5 grams for a 99 percent yield of clear, very viscous polyester.

EXAMPLE XX

The products of Examples I through XIX did not burn or support combination; even the copolymers of Examples IX, X, XII, XIII, and XV were self-extinguishing.

A mixture of 2 grams of the unsaturated polyester formed in Example XIX and 2 grams of styrene was warmed at 80° C. to effect solution, then heated with 0.01 grams of benzoyl peroxide at 100°–110° C. for 2 hours to give a clear, hard resin that did not burn.

EXAMPLE XXI

Mixed polyesters are prepared from ethylene glycol and terephthalic acid with 5-(1-methyl-3,4,5,6,7,7-hexachloro-norborn-4-ene-1)-isophthalic acid dichloride. The acid and the acid dichloride are mixed in proportions in the ranges of from 10 percent up to 75 percent terephthalic acid, from 25 percent up to 90 percent 5-(1-methyl-3,4,5,6,7,7-hexachloro-norborn-4-ene-1)-isophthalic acid dichloride. The molar ratio of ethylene glycol to the mixture of the acid and acid dichloride is 1:1. The reactions proceeds by a condensation well known in the art. The polyesters thus prepared do not burn or support combustion.

EXAMPLE XXII

Mixed polyamides are prepared from the 1,6-hexanediamine and adipic acid with 5-(1-methyl-3,4,5,6,7,7-hexachloro-norborn-4-ene-1)-isophthalic acid dichloride. The acid and acid chloride are mixed in proportions in the ranges of from 10 percent up to 80 percent 1,6-hexanediamine, from 20 percent up to 90 percent 5-(1-methyl-3,4,5,6,7,7-hexachloro-norborn-4-ene-1)-isophthalic acid dichloride. The molar ratio of 1,6-hexanediamine to the mixture of the acid and acid dichloride is 1:1. The reaction proceeds by a condensation well known in the art. The polyamides thus prepared do not burn or support combustion.

EXAMPLE XXIII

The products of Examples XVII and XVIII were tested as extreme-pressure additives in 5W oil on the Almen machine (which is described in Almen, U.S. 2,001,861 (1935)), with these results:

| Additive | | Pass, lbs. | Fail, lbs. |
|---|---|---|---|
| 0 | | 4 | 6 |
| 1% | Example 17 | 16 | 18 |
| 1% | Example 18 | 30+ | — |
| 0.5% | ″ | 30+ | — |
| 0.2% | ″ | 30+ | — |
| 0.1% | ″ | 14 | 16 |

The products of this invention can be used in oils at concentrations of 0.001 to 10 percent by weight.

What is claimed is:
1. A compound having the structure

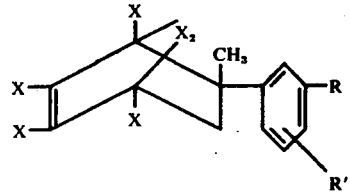

wherein each X is halogen, R and R' are alkyl groups and R' is either in the 4 or 5 position.
2. The compound of claim 1 wherein each halo group is bromo.
3. The compound of claim 1 wherein each halo group is chloro.
4. A method for producing the Diels-Alder adduct of claim 1 comprising
mixing hexabromocyclopentadiene or nexachlorocyclopentadiene and 3,5-dialkyl-α-methylstyrene or 3,4-dialkyl-α-methylstyrene in a molecular ratio ranging from about 1:5 to about 5:1;
heating the mixture to a temperature in the range from 80° C. to 180° C., for 1 hour to 24 hours at a pressure of from 15 pounds per square inch to 300 pounds per square inch;
distilling the mixture in vacuo at a pressure in the range of from 0.1 millimeter to 2 millimeters until the temperature of the reaction mixture is from 85° C. to 140° C; and
recrystallizing the adduct product crystals produced during distillation from a nonpolar solvent.
5. The method of claim 4 wherein hexabromocyclopentadiene or hexachlorocyclopentadiene is mixed with 3,5-dialkyl-α-methylstyrene or 3,4-dialkyl-α-methylstyrene in a molecular ratio of 1:1; and wherein the mixture is heated to a temperature in the range from 135° C. to 160° C. from 3 hours to 15 hours at a pressure of 10 pounds per square inch; and wherein the mixture is distilled in vacuo at a pressure in the range of 0.5 millimeter to 1 millimeter until the temperature of the mixture is between 100° C. and 120° C.

* * * * *

UNITED STATES PATENT OFFICE
CERTIFICATE OF CORRECTION

Patent No. 4,025,569                    Dated May 24, 1977

Inventor(s) ELLIS K. FIELDS AND MARGARET M. STEITZ

It is certified that error appears in the above-identified patent and that said Letters Patent are hereby corrected as shown below:

In the patent:

Column 2, line 16 is: "3,4-dialkyl-60-methylstyrene" and should read

--3,4-dialkyl-$\alpha$-methylstyrene--.

Column 3, line 16 is: "400 per square inch" and should read --400 pounds per square inch.

Column 4, line 3 is: "weighted" and should read --weighed--.
Column 5, line 33 "95 - percent" should read --95 percent--.
Column 5, line 35 "5-(-methyl-3,4,5,6,7,7-" and should read --5-(1-methyl-3,4,5,6,7,7--.

Column 7, line 3 is "254°C" and should read --245°C--.

Column 7, line 61 is: "$C_{13}H_{20}O_4Cl_8$" and should read --$C_{31}H_{20}O_4Cl_8$--.

Column 10, line 61 shows the _last_ paragraph of Example XVII appearing as the _first_ paragraph of Example XVIII.

UNITED STATES PATENT OFFICE
CERTIFICATE OF CORRECTION

Patent No. 4,025,569      Dated May 24, 1977

Inventor(s) ELLIS K. FIELDS AND MARGARET M. STEITZ

It is certified that error appears in the above-identified patent and that said Letters Patent are hereby corrected as shown below:

Column 11, line 6 is: "26.4% and" and should read --26.4% P and --.

Column 11, line 10 is: "As unsaturated" and should read --An unsaturated--.

Column 11, line 24 is "combination;" and should read --combustion;--.

In the claims, Claim 4, column 12, line 38 is: "nexachlorocyclopentadiene" and should read --hexachlorocyclopentadiene--.

Signed and Sealed this

Twenty-eighth Day of March 1978

[SEAL]

Attest:

RUTH C. MASON
*Attesting Officer*

LUTRELLE F. PARKER
*Acting Commissioner of Patents and Trademarks*